US009693801B2

(12) United States Patent
Allen

(10) Patent No.: US 9,693,801 B2
(45) Date of Patent: Jul. 4, 2017

(54) RELEASABLY SECURABLE NEEDLE AND HANDLE SYSTEM AND METHOD

(71) Applicant: AMS RESEARCH CORPORATION, Minnetonka, MN (US)

(72) Inventor: John J. Allen, Mendota Heights, MN (US)

( * ) Notice: Subject to any disclaimer, the term of this patent is extended or adjusted under 35 U.S.C. 154(b) by 208 days.

(21) Appl. No.: 14/377,149

(22) PCT Filed: Feb. 13, 2013

(86) PCT No.: PCT/US2013/025920
§ 371 (c)(1),
(2) Date: Aug. 6, 2014

(87) PCT Pub. No.: WO2013/123036
PCT Pub. Date: Aug. 22, 2013

(65) Prior Publication Data
US 2014/0378757 A1 Dec. 25, 2014

Related U.S. Application Data

(60) Provisional application No. 61/598,198, filed on Feb. 13, 2012.

(51) Int. Cl.
*A61B 17/34* (2006.01)
*A61F 2/00* (2006.01)
*A61B 17/06* (2006.01)
*A61B 17/00* (2006.01)

(52) U.S. Cl.
CPC .... *A61B 17/3468* (2013.01); *A61B 17/06109* (2013.01); *A61F 2/0045* (2013.01); *A61B 2017/0046* (2013.01); *A61B 2017/00469* (2013.01); *A61B 2017/00805* (2013.01); *A61B 2017/347* (2013.01)

(58) Field of Classification Search
CPC ............ A61F 2/0045; A61B 17/06109; A61B 2017/00805; A61B 2017/0046; A61B 2017/00469; A61B 2017/347; A61B 17/3468
See application file for complete search history.

(56) References Cited

U.S. PATENT DOCUMENTS

2002/0099259 A1* 7/2002 Anderson ............. A61F 2/0045
600/29
2004/0144395 A1* 7/2004 Evans ............. A61B 17/06066
128/885

* cited by examiner

*Primary Examiner* — Christine H Matthews
*Assistant Examiner* — Joshua D Lannu
(74) *Attorney, Agent, or Firm* — Brake Hughes Bellermann LLP

(57) ABSTRACT

An implant and needle delivery system including a needle selectively releasable from a handle assembly is provided. The needle is selectively connectable with an elongate sling and the needle is selectively releasable from the handle assembly an implantation procedure to treat a pelvic disorder or condition, such as incontinence.

21 Claims, 9 Drawing Sheets

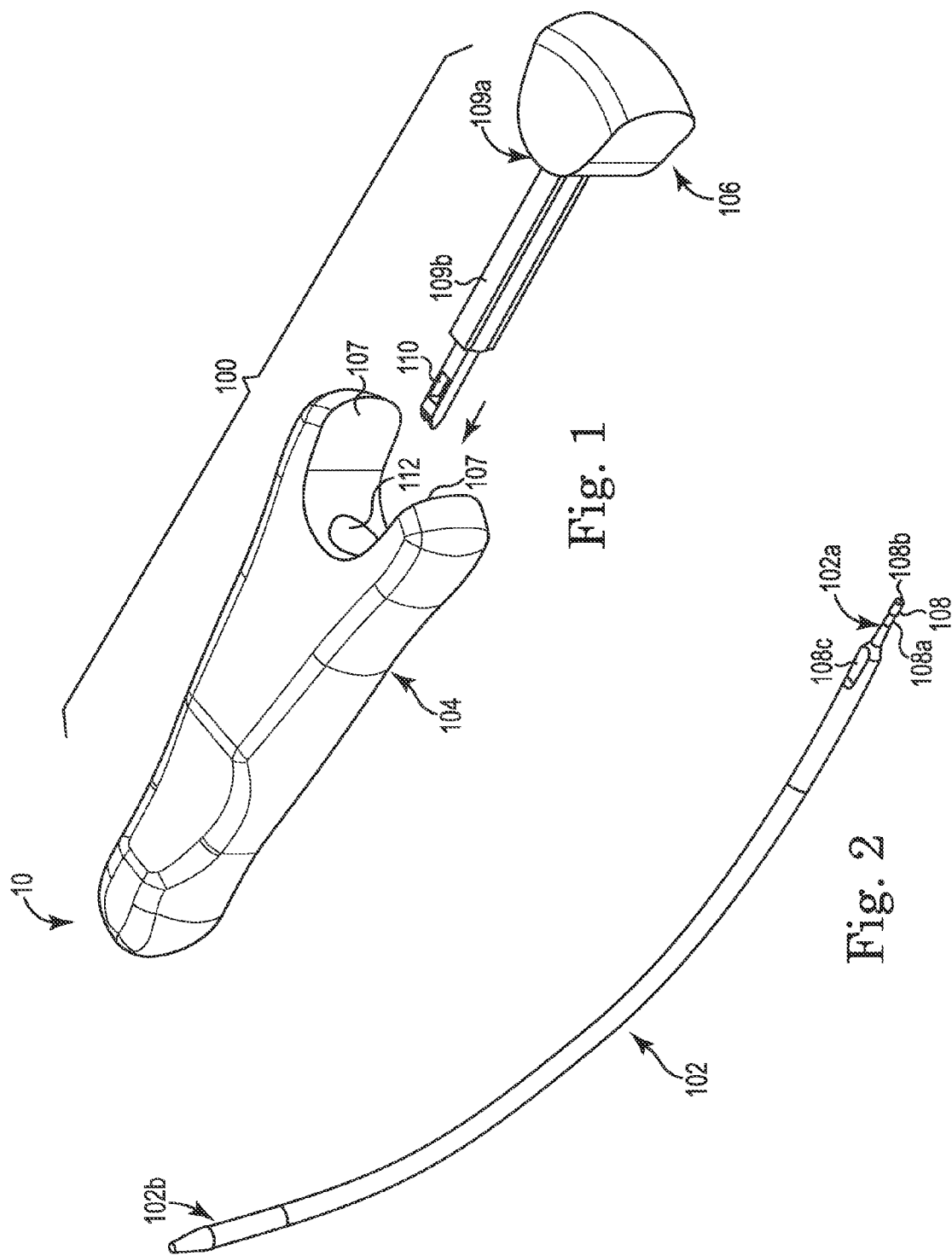

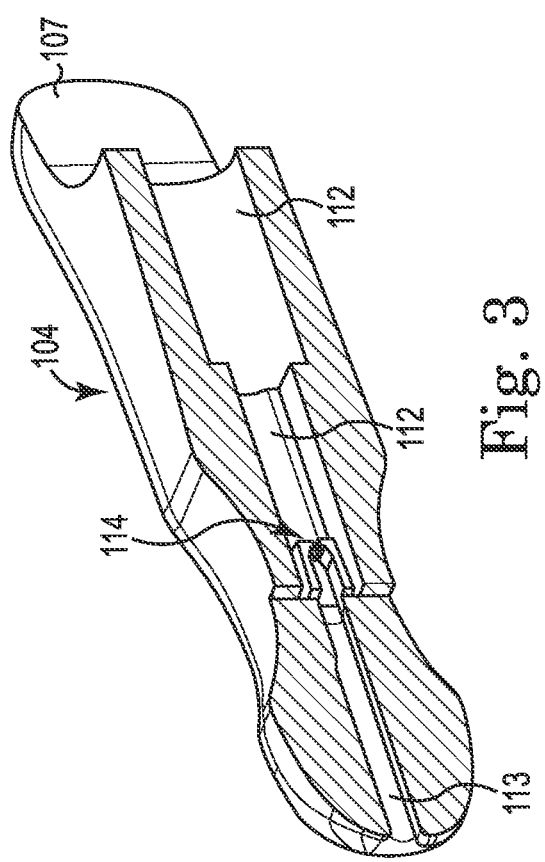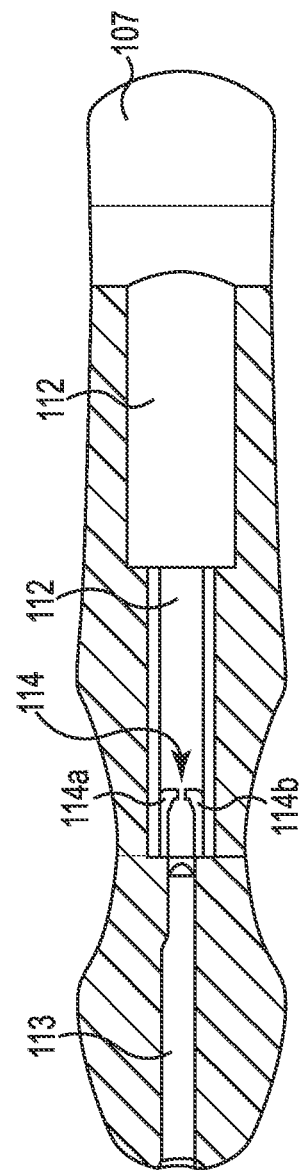

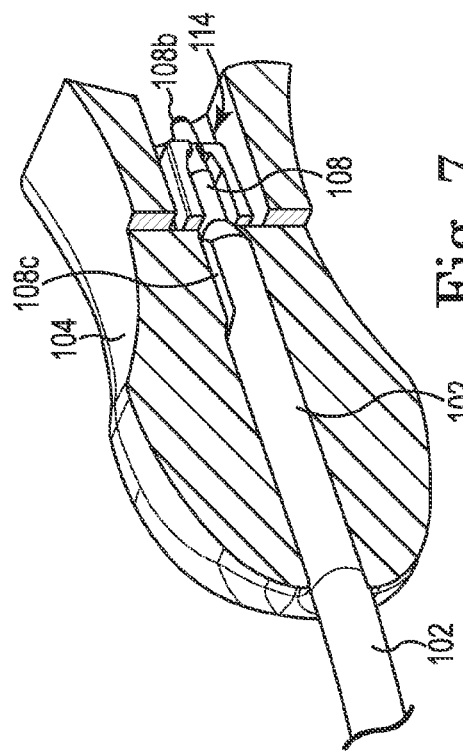
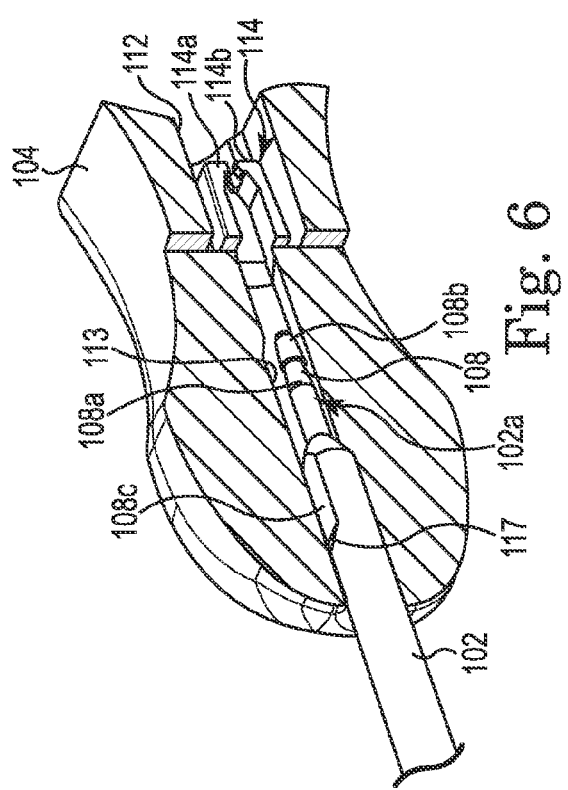
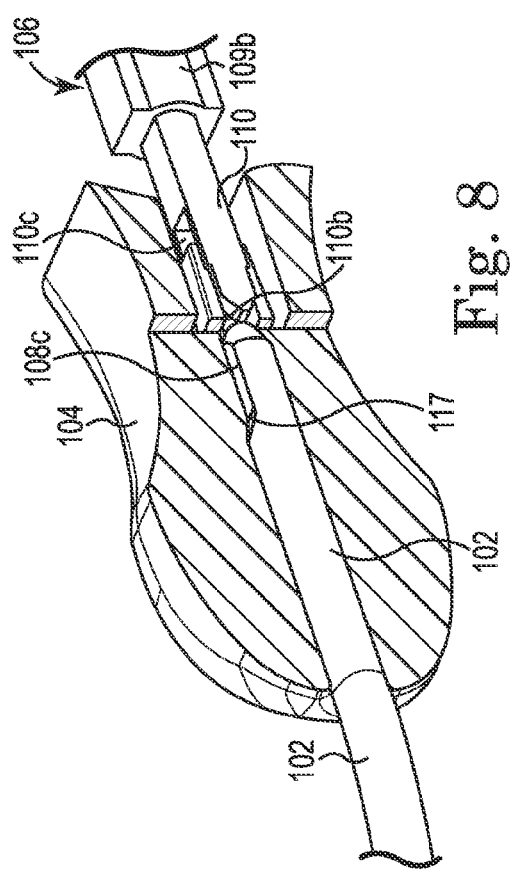

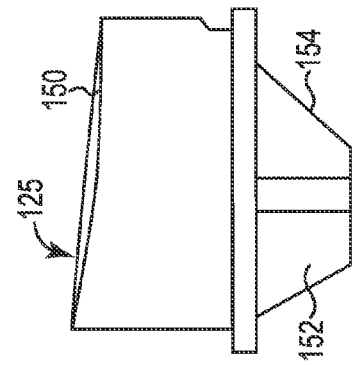
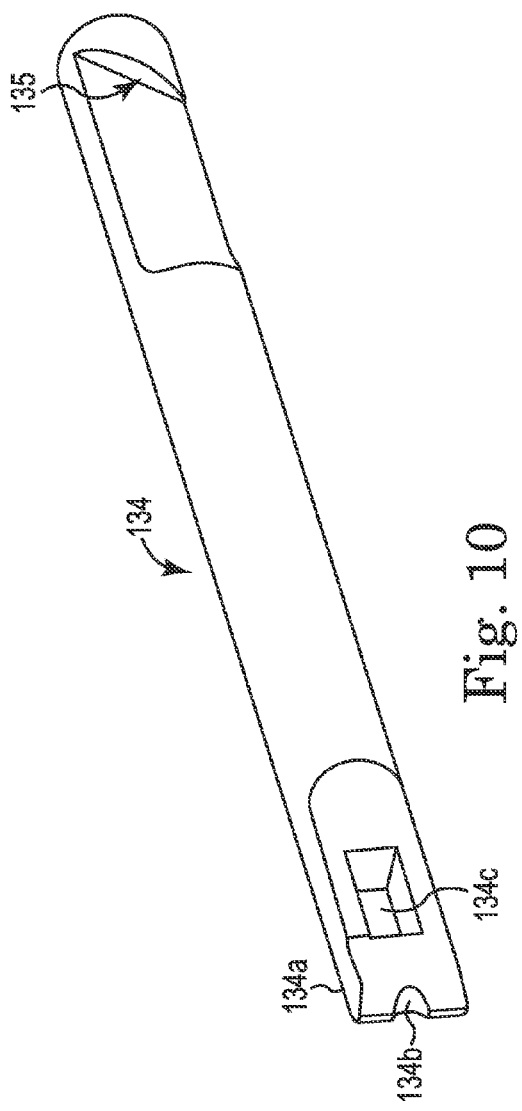
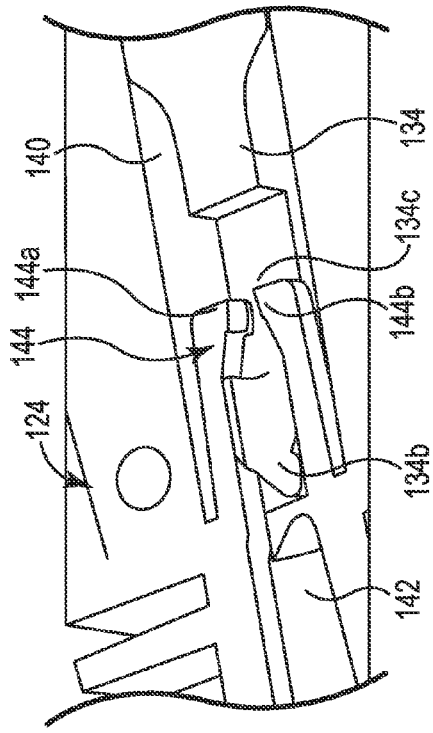

RELEASABLY SECURABLE NEEDLE AND HANDLE SYSTEM AND METHOD

PRIORITY

This application claims priority to and the benefit of U.S. Provisional Patent Application No. 61/598,198, filed Feb. 13, 2012, which is incorporated herein by reference in its entirety.

FIELD OF THE INVENTION

The present invention relates generally to surgical methods and apparatus and, more specifically, to a rapid release needle connector for retropubic sling trocars to provide needle separation during a sling implantation procedure to treat incontinence or other pelvic disorders.

BACKGROUND OF THE INVENTION

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Urinary incontinence can be characterized by the loss or diminution in the ability to maintain the urethral sphincter closed as the bladder fills with urine. Male or female stress urinary incontinence (SUI) occurs when the patient is physically stressed.

A variety of treatment options are currently available to treat incontinence. Some of these treatment options include external devices, behavioral therapy (such as biofeedback, electrical stimulation, or Kegal exercises), injectable materials, prosthetic devices and/or surgery. Depending on age, medical condition, and personal preference, surgical procedures can be used to completely restore continence. One type of procedure, found to be an especially successful treatment option for SUI in both men and women, is a sling procedure.

A sling procedure is a surgical method involving the placement of a sling to stabilize or support the bladder neck or urethra. There are a variety of different sling procedures. Slings used for pubovaginal procedures differ in the type of material and anchoring methods. In some cases, the sling is placed under the bladder neck and secured via suspension sutures to a point of attachment (e.g. bone) through an abdominal and/or vaginal incision. Suprapubic approaches are also known, such as SPARC from American Medical Systems. In such approach, a narrow sling carrier is passed from above the pubic bone to the vagina. The sling mesh then is attached to the carriers and pulled into place. A self-fixating polypropylene sling cradles the urethra and gives it support during normal daily activities.

There is a desire to provide an improved handle, system and method for releasably attaching the needle elements to the handle for use in retropubic sling implantation procedures.

SUMMARY OF THE INVENTION

The present invention provides a handle assembly and trocar needle attachment mechanism, system and method for sling implantation. The handle assembly is selectively attachable and detachable with the needle to facilitate retropubic, or "inside-out," sling implantation procedures.

The handle assembly can include a handle body portion and a release sleeve in certain embodiments. The needle can be curved, and can include a proximal end portion and a distal end portion. The proximal end includes a tip that can be releasably secured in the handle assembly. In certain embodiments, the tip can include one or more circumferential indents, grooves or angled surfaces and a bulbous end portion. A pocket or recess portion of the handle body is adapted to mateably receive the sleeve. The sleeve can include a body portion and an elongate shaft portion. The elongate shaft portion can include a retention end arm feature, and the body portion can be shaped and sized to mateably seat within the recess portion of the handle body. The end arm feature of the sleeve can include a distal tip and an aperture extending a distance into the distal tip. Further, an opening can be provided extending into a surface of the feature and in fluid communication with the aperture. A portion of a channel of the handle body can include a retention clip having opposing fingers configured to extend inward within the channel. The needle tip is inserted in an axial direction into the channel of the handle body until the tip snaps into place within the confines of the fingers of the retention clip. Axial pulling on the sleeve can deform or otherwise release the fingers of the retention clip to thereby facilitate release of the needle from the handle assembly.

In other embodiments, the needle can be secured in the handle and then released by pressing a release actuator, such as a button, thus displacing the needle away from engagement with the handle. The actuator can include a top portion and a bottom portion. The bottom portion can include one or more angled edges or surfaces adapted to engage with the arm. For instance, the arm can include a ramp feature (e.g., angled surface), wherein depressing or otherwise actuating the button causes the button to move down such that the angled edge of the bottom portion engages with and slides down along the ramp feature of the arm. This, in turn, pushes or axially directs the arm within the channel back away from the clip. As the arm traverses back and is pulled out of engagement with the clip, the fingers are spread out or displaced as they slide out of or otherwise disengage from the opening of the arm. Once the fingers are separated a sufficient distance, their secure engagement with the bulbous tip is correspondingly released enough to permit the needle (e.g., tip) to slide away or otherwise disengage from the securement of the clip. The handle can then be slid back away from the needle, or the needle can be slid or pulled away from the channel, and the handle in general.

Various sling or implant devices can be employed for use with the releasable delivery needle and handle systems disclosed herein. A sling assembly can include an elongate mesh implant, such as a polypropylene monofilament mesh. A tensioning suture (e.g., absorbable) is threaded into or along the length of the mesh implant. A pair of polymer or like sheaths cover and protect the mesh implant during deployment and placement. The sheaths, in certain embodiments, overlap at or proximate the center of the assembly, as indicated by a center marking (e.g., blue). One or more connectors are provided at the ends of the assembly and are adapted to connect to ends of the various delivery needles of the present invention during the procedure. One or more additional marking (e.g., blue) are provided near the end regions of the assembly or sheaths, identifying where to cut the sling assembly to allow the sheaths to be removed after placement of the mesh implant.

BRIEF DESCRIPTION OF THE DRAWINGS

FIG. 1 is an exploded view of a handle assembly having a release sleeve, in accordance with embodiments of the present invention.

FIG. 2 is a perspective view of a delivery needle for insertion and selective release from the handle assembly of FIG. 1, in accordance with embodiments of the present invention.

FIGS. 3-4 are cross-section schematic views of a handle body, in accordance with embodiments of the present invention.

FIGS. 6-8 are partial cross-section schematic views of needle and retention arm securement with a retention clip within a handle body, in accordance with embodiments of the present invention.

FIG. 10 is a perspective view of a release arm of a handle body, in accordance with embodiments of the present invention.

FIG. 11 is a perspective view of a button actuator of a handle body, in accordance with embodiments of the present invention.

FIG. 12 is a partial cross-section schematic view of securement of a release arm with a retention clip of a handle body, in accordance with embodiments of the present invention.

DETAILED DESCRIPTION OF PREFERRED EMBODIMENTS

Figure 5:
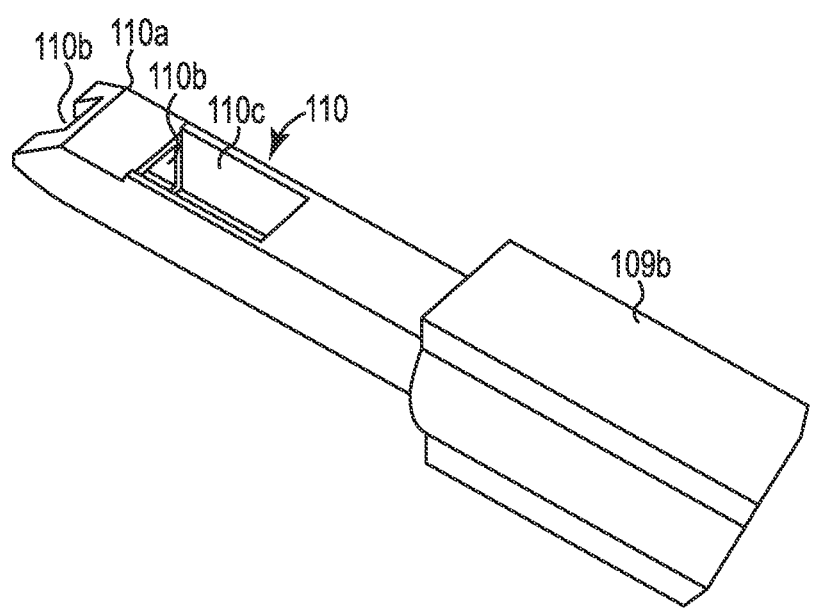
FIG. 5 is a partial perspective view of an elongate shaft and retention arm feature of a release sleeve, in accordance with embodiments of the present invention.
Figure 9:
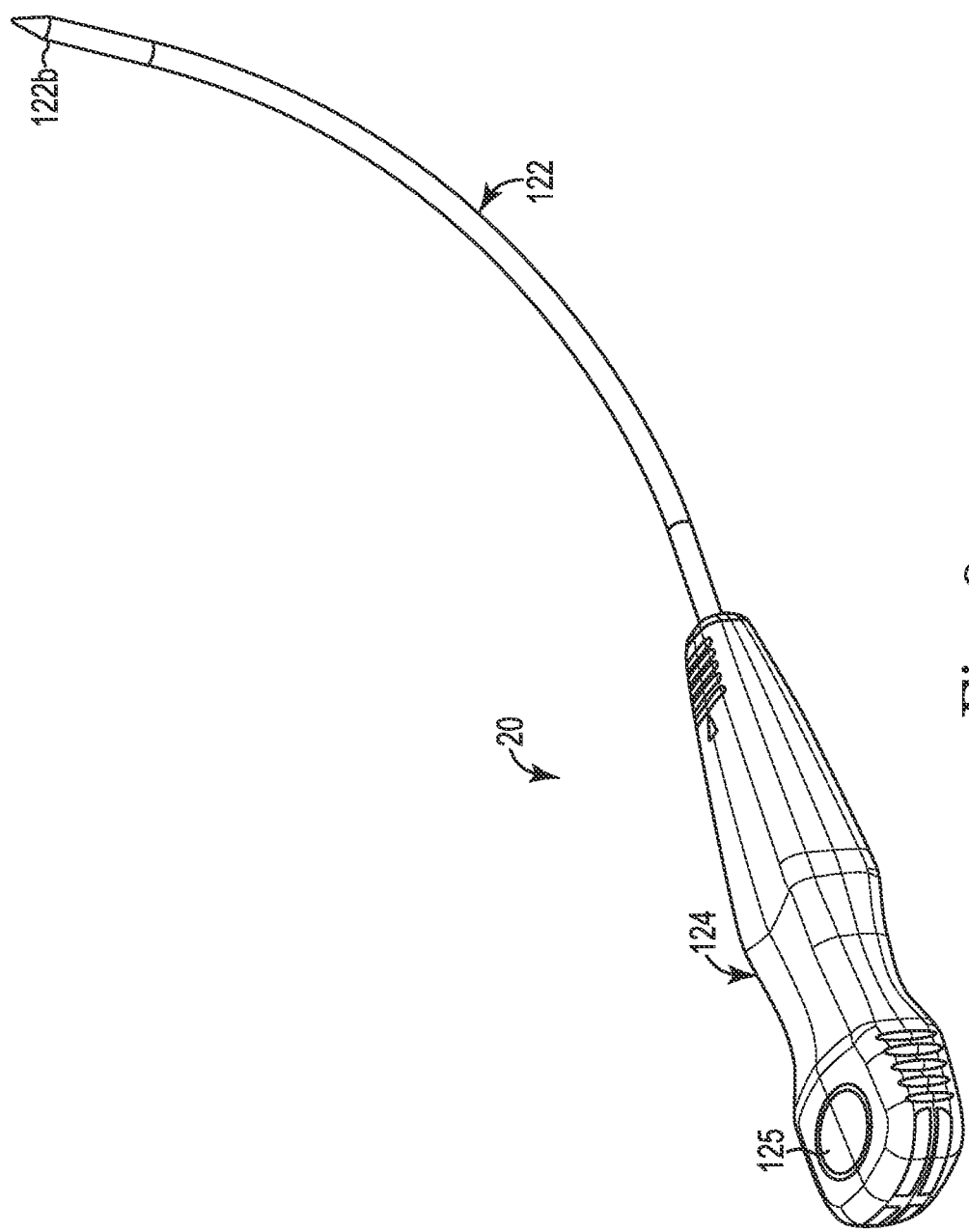
FIG. 9 is a perspective view of a handle and releasably securable needle system, in accordance with embodiments of the present invention.
Figure 13:
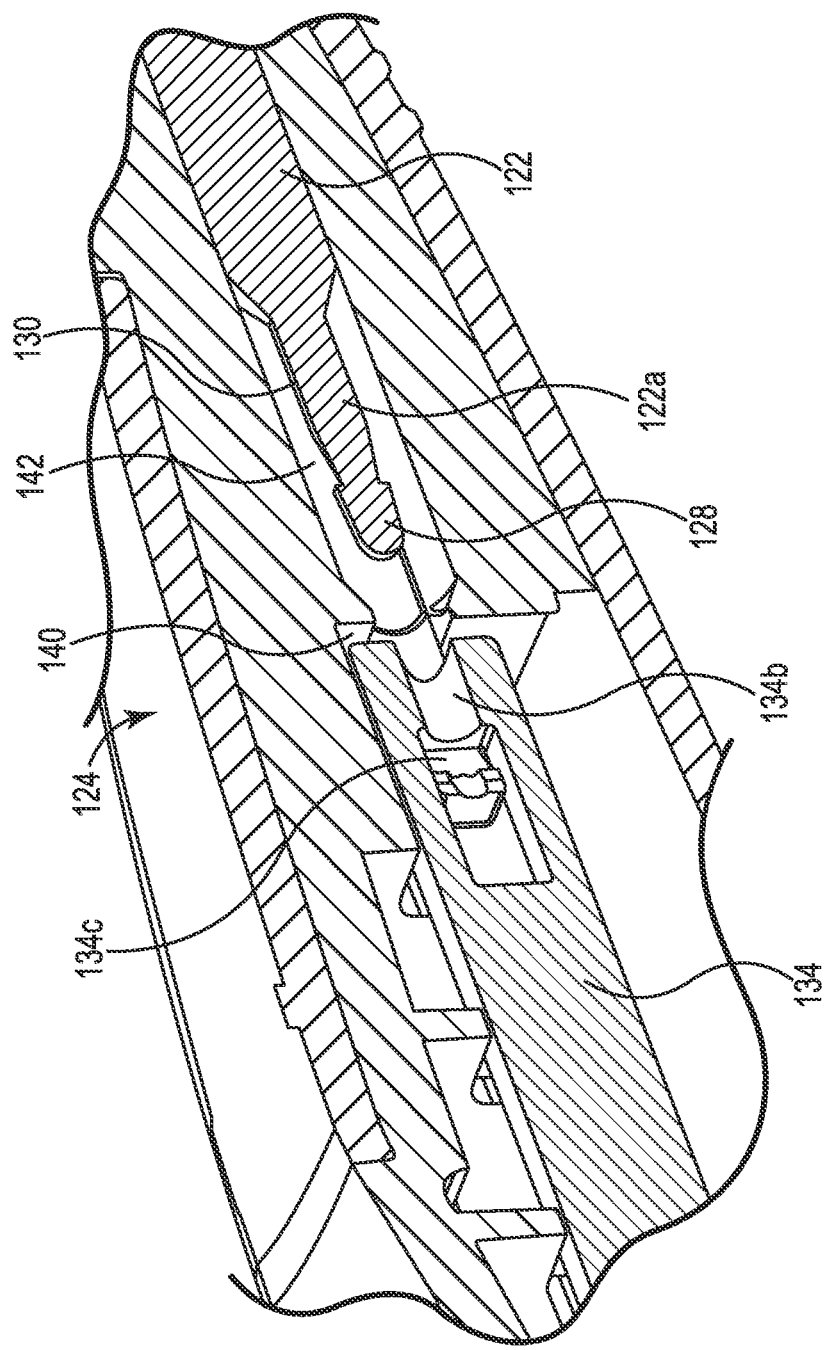
FIGS. 13-14 are partial cross-section schematic views of needle and retention arm securement with a retention clip within a handle body, in accordance with embodiments of the present invention.

Referring generally to FIGS. 1-16, releasable needle systems 10 and methods are shown. Various embodiments of the system 10 can include a handle assembly 100 and a trocar needle 102.

As shown in FIGS. 1-8, embodiments of the handle assembly 100 can include a handle body portion 104 and a release sleeve 106. The needle 102 can be curved, and includes a proximal end portion 102a and a distal end portion 102b. The proximal end 102a includes a tip 108 that can be releasably secured in the handle assembly 102 as disclosed herein. The tip 108 can include one or more recesses, indents, protrusions, grooves or like features to facilitate securement and release of the needle 102 from the handle 104. For instance, in certain embodiments, the tip 108 can include one or more circumferential indents, grooves or angled surfaces 108a and a bulbous end portion 108b. The proximal end portion 102a can further include one or more recessed flats 108c or like structures, with the one or more features 108a provided intermediate the flat 108c and the end portion 108b. The tip 108 or other portions of the needle 102 can be constructed of metal or a composite material, or an injection molded plastic.

Referring to FIGS. 1-5, the handle body 104 can be generally tapered or angled outward where the release sleeve 106 is selectively received. A pocket or recess portion 107 is adapted to mateably receive the sleeve 106. The sleeve 106 can include a body portion 109a and an elongate shaft portion 109b, as demonstrated in FIGS. 1 and 5. The elongate shaft portion 109b can include a retention end arm feature 110, and the body portion 109a can be shaped and sized to mateably seat within the recess portion 107 of the handle body 104. The end arm feature 110 of the sleeve 106 can include a distal tip 110a and an aperture 110b extending a distance into the distal tip 110a. Further, an opening 110c can be provided extending into a surface of the feature 110 and in fluid communication with the aperture 110b, as shown in FIG. 5.

The handle body 104 includes a retention channel 112 adapted to receive the retention end feature 110 and the elongate shaft portion 109b of the sleeve 106, along a first length of the channel 112 extending in from the portion 107, with the channel 112 further extending into and through the opposing end of the body 104 to define a needle channel 113. As shown in FIGS. 3-4, the channel 112 can be larger at the end of the handle body 104 having the recess portion 107 and then narrow a distance within the body 104. A portion of the channel 112 can include a retention clip 114 having opposing fingers 114a, 114b. The fingers 114a, 114b can include lips, protrusions, angled features and the like, and can be configured to extend inward within the channel 112, as shown in FIG. 4.

As shown in FIGS. 6-8, operation of the handle assembly 102 can include inserting the needle tip 108 in an axial direction into the channel 113 of the handle body 104 (FIG. 6). The axial movement continues until the tip 108 snaps into place within the confines of the fingers 114a, 114b of the retention clip 114, as shown in FIG. 7.

For example, the bulbous tip 108b is pushed through the gap between the fingers 114a, 114b, causing the fingers to displace or deform a measurable amount and then snap or otherwise return to the initial opposing state once the bulbous tip 108b is beyond the fingers 114a, 114b. This will selectively secure the needle tip 108 within the retention clip 114. Note that the release sleeve 106 is not shown in FIG. 7 to improve clarity of the depiction. However the sleeve would normally be present, as shown in FIG. 8. Namely, the feature 110 of the sleeve 106 is inserted through the channel 112 to a position where the fingers 114a, 114b extend into the opening 110c and the needle tip 108 extends into the aperture 110b of the feature 110 for snapping engagement with the fingers 114a, 114b as described herein. Once secured or locked in place, the needle tip 108 generally cannot be pulled out unless it is released by an axial pull on the release sleeve 106 in a direction away from the needle. Namely, to release the needle 102 from the handle 100, the sleeve 106 is pulled back away from the handle body 104 such that the fingers 114a, 114b are spread out, deformed or displaced as they slide out of or otherwise disengage from the opening 110c of the feature 110. Once the fingers 114a, 114b are separated a sufficient distance, their secure engagement with the tip 108 is correspondingly released enough to permit the needle 102 (e.g., tip 108b) to slide away or otherwise disengage from the securement of the clip 114. The handle 104 can then be slid back away from the needle 102, or the needle 102 can be slid or pulled away from the channel 113, and the handle 104 in general.

One or more components of the handle assembly 100 can be constructed of a plastic material and can be fabricated via injection molding or other processes. A two-shot process or overmolding with an elastomeric skin layer such as Santoprene can be performed without departing from the scope of the invention. Moreover, components or portions of the handle can be formed from metal or composite materials, or by using different manufacturing processes without departing from the invention scope.

In certain embodiments, rotational stability of the needle 102 is maintained while it is secured in the handle assembly 100. Minor angular play at the connector tip 102a can translate to large, undesirable movement at the opposing distal end 102b of the needle as it passes through the patient's tissues or is otherwise deployed or introduced. Such movement could result in misdirection of the distal tip 102b. Thus, the one or more flat portions 108c on the needle 102 mate with respectively-shaped features or surfaces in the channel 113 of the handle to enhance torsional stability, as shown in FIGS. 6-8. The flat portions of the channel 113 and needle 108c closely conform to one another and can slightly interfere. In certain example embodiments, the tolerance could be +0.0005/−0.0010 inches (with + being interference). These tolerance parameters are exemplary and other tolerance values and parameters can be applied without departing from the scope of the invention.

In another aspect of the invention, certain performance characteristics can be provided for the portions, components or features of the handle assembly 100. In one embodiment, the clip feature 114 can comprise RTP 305 polycarbonate (PC), which is 30% glass filled. In such an embodiment, a tensile modulus of $1.20 \times 10^6$ psi, a tensile strength of 18000 psi and a flexural strength of 28500 psi can be achieved. In general, the configuration and materials provide a retention system where a metal needle body 102 may bear the highest stress, but such loads are well below its yield strength. The deflection and stress on the body of the handle is minimal.

With various embodiments, initial introduction of the release sleeve 106 into the body 104 portion forces the fingers 114a, 114b to spread apart by a deflection of approximately 0.040 inches. This can be greater than the deflection required to release the needle 102, so repeated insertion/releases of the needle 102 produces lower stresses. The upward force required to generate the 0.040 inch deflection of the fingers can be approximately three pound-foot. Assuming that the deflection to release the needle is no more than 0.025 inches in certain embodiments, the maximum deflection force per finger (e.g., 114a or 114b) of the clip 114 can be about 1.88 pound-foot. If the pulling force is too large for finger grip actuation, then the load can be reduced by modifying the part (e.g., fingers 114a, 114b) geometry or using a weaker resin material.

Referring to FIGS. 9-14, another embodiment of a releasable needle system 20 is shown. A needle 122 can be secured in a handle 124 and then released by pressing a release actuator 125, such as a button, thus displacing the needle 122 away from engagement with the handle 124.

Like other embodiments, the needle 122 can be curved, and includes a proximal end 122a and a distal end 122b. The proximal end 122a includes a tip that can be releasably secured in the handle 124 as disclosed herein. The tip can include one or more recesses, indents, protrusions, grooves or like features to facilitate securement and release of the needle 122 from the handle 124. For instance, in certain embodiments, the tip at the proximal end 122a can include one or more circumferential indents, grooves or angled surfaces, and a bulbous end portion 128. The proximal end 122a can further include one or more recessed flats 130 to assist in preventing rotational movement of the needle 122 within the handle 124. The end portion 128 or other portions of the needle 122 can be constructed of metal or a composite material, or of an injection molded or like polymer material.

Referring to FIGS. 10-12, the handle 124 can include a release assembly 132. The release assembly can include a release arm 134, the actuator 125, and a biasing member, such as a spring. The release arm 134, like the retention end feature 110 of other embodiments, is generally elongate and can include a distal retention tip 134a and an aperture 134b extending a distance into the distal tip 134a. Further, an opening 134c can be provided extending into a surface of the arm 134 and in fluid communication with the aperture 134b.

The handle 124 further includes a retention channel 140 adapted to receive the retention arm 134, with the channel 140 further extending into and through the opposing end of the handle 124 to define a needle channel 142. A portion of the channel 140 can include a retention clip 144 having opposing fingers 144a, 144b. The fingers 144a, 144b can include lips, protrusions, angled features and the like, and can be configured to extend inward within the channel 140, as shown in FIG. 12.

Figure 14:
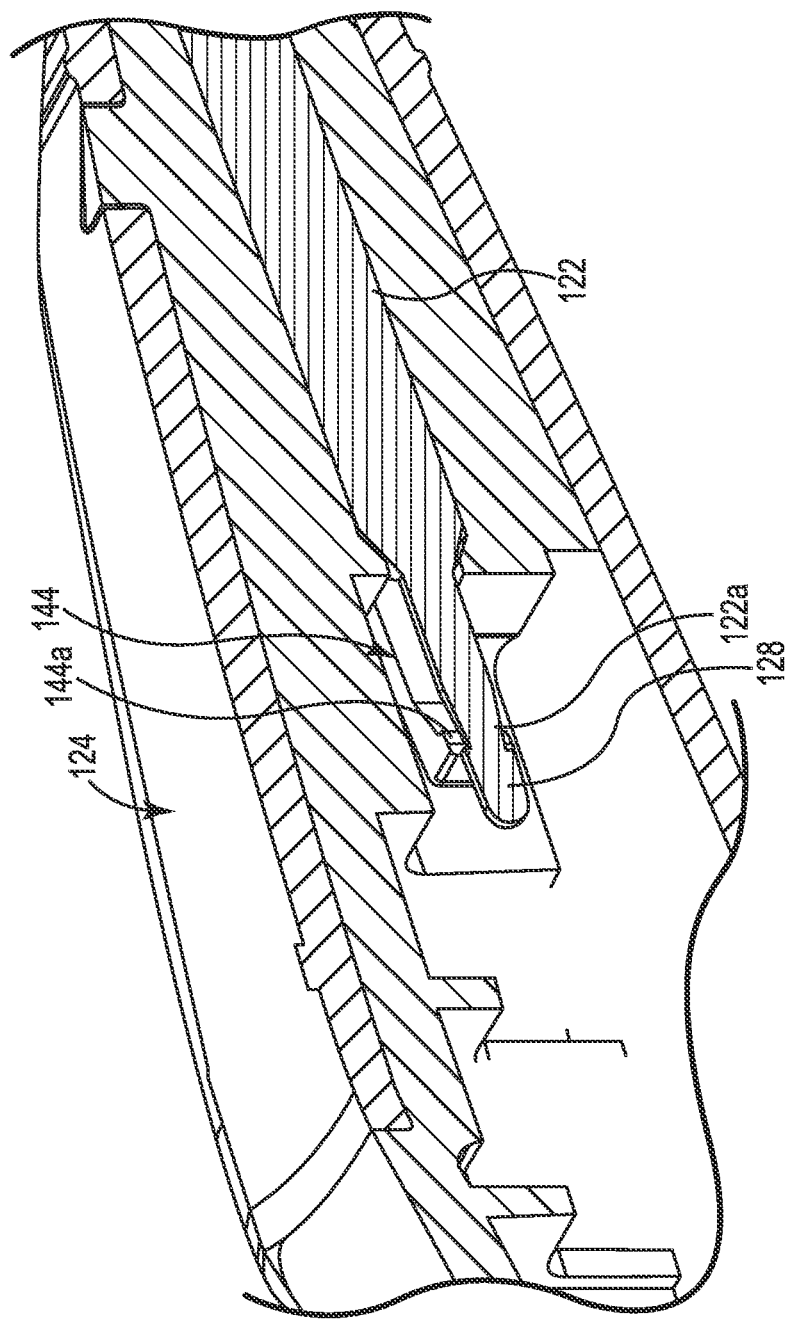

As shown in 12-14, operation of the handle 124 can include inserting the needle tip 122a in an axial direction into the channel 142 of the handle 124. The axial movement continues until the bulbous end 128 snaps into place or otherwise secures within the confines of the fingers 144a, 144b of the retention clip 144 (FIG. 14).

Again, the bulbous tip 128 is pushed through the gap between the fingers 144a, 144b, causing the fingers to displace or deform a measurable amount and then snap or otherwise return to the initial opposing state once the bulbous tip 128 is beyond the fingers 144a, 144b. This will selectively secure the needle end 122a within the retention clip 144. While the needle end 122a is being inserted, the retention arm 134 is already in place and engaged with the clip 144, as described with other embodiments. Namely, the arm 134 is provided within and is adapted to traverse axially within the retention channel 140, with the fingers 144a, 144b selectively extendable into the opening 134c and the needle end 122a extends into the aperture 134b of the arm 134 for snapping engagement of the bulbous tip 128 with the fingers 144a, 144b as described herein. Once secured or locked in place, the needle end 122a generally cannot be pulled out unless it is released by actuation or other engagement of the actuator 125.

The actuator 125, as shown in FIG. 11, can be a button or like device with a top portion 150 and a bottom portion 152, such that the spring generally biases it in the extended position away from the handle 124. The bottom portion 152 can include one or more angled edges or surfaces 154 adapted to engage with the arm 134. For instance, the arm 34 can include a ramp feature (e.g., angled surface) 135 (FIG. 10), wherein depressing or otherwise actuating the button 125 causes the button 125 to move down such that the angled edge 154 of the bottom portion 152 engages with and slides down along the ramp feature 135 of the arm 134. This, in turn, pushes or axially directs the arm 134 within the channel 140 back away from the clip 144. As the arm 134 traverses back and is pulled out of engagement with the clip 144, the fingers 144a, 144b are spread out, deformed or displaced as they slide out of or otherwise disengage from the opening 134c of the arm 134. Once the fingers 144a, 144b are separated a sufficient distance, their secure engagement with the bulbous tip 128 is correspondingly released enough to permit the needle 122 (e.g., tip 128) to slide away or otherwise disengage from the securement of the clip 144. The handle 124 can then be slid back away from the needle 122, or the needle 122 can be slid or pulled away from the channel 142, and the handle 124 in general.

The various exemplary characteristics, tolerances, dimensions and properties of the handle and/or needle components of the previously-disclosed embodiments can be used to create, or make up this actuator embodiment of the present invention.

Figure 15:
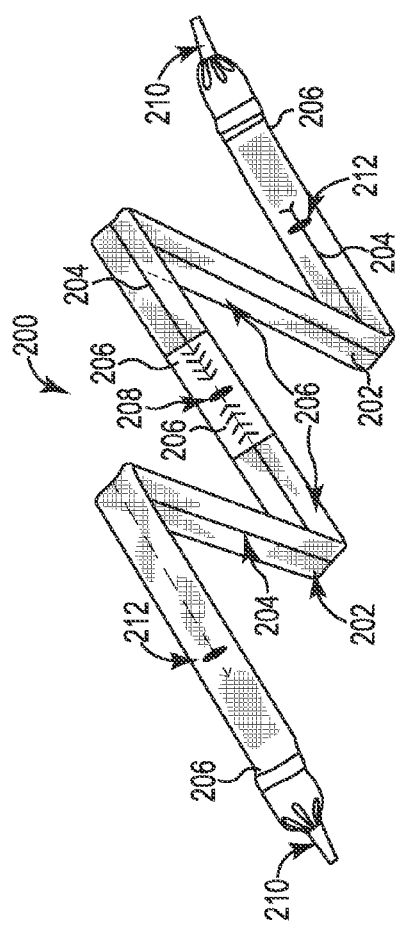
FIG. 15 is a perspective view of a sling implant assembly, in accordance with embodiments of the present invention.

Various sling or implant devices can be employed for use with the releasable delivery needle and handle systems disclosed herein. For instance, in one embodiment, a sling assembly 200 is shown in FIG. 15. The sling assembly 200 can include an elongate mesh implant 202, such as a polypropylene monofilament mesh. In certain embodiments, the mesh implant 202 is approximately 1.1 cm wide by 50 cm in length. A tensioning suture 204 (e.g., absorbable) is threaded into or along the length of the mesh implant 202. A pair of polymer or like sheaths 206 cover and protect the mesh implant 202 during deployment and placement. The sheaths 206, in certain embodiments, overlap at or proximate the center of the assembly 200, as indicated by a center marking (e.g., blue) 208. One or more connectors 210 are provided at the ends of the assembly 200 and are adapted to connect to ends of the various delivery needles of the present invention during the procedure. One or more additional marking (e.g., blue) 212 are provided near the end regions of the assembly 200 or sheaths 206, identifying where to cut the sling assembly 200 to allow the sheaths 206 to be removed after placement of the mesh implant 202.

The following is an exemplary procedure for using the various releasable needle and handle systems disclosed herein with a retropubic sling assembly 200 to treat stress urinary stress incontinence or like pelvic disorders or conditions.

Figure 16:
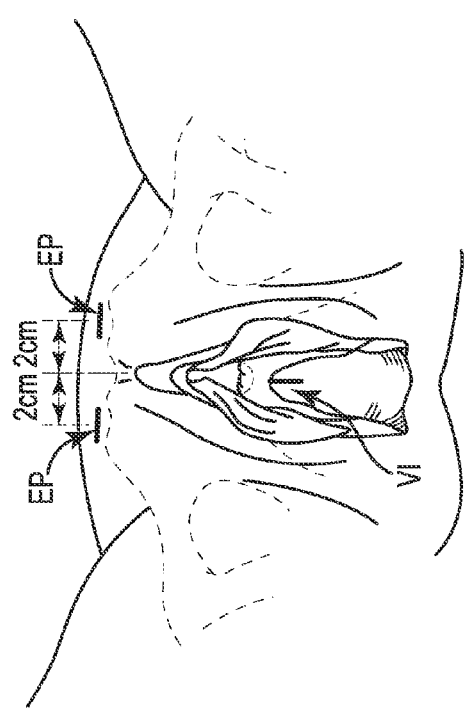
FIG. 16 is an illustrative view of vaginal and abdominal surgical incision locations for a retropubic incontinence treatment procedure, in accordance with embodiments of the present invention.

First, the patient can be placed in a modified dorsal lithotomy position with hips flexed, legs elevated in stirrups and buttocks even with the edge of the table. Next, the physician can identify and mark the two suprapubic exit points EP approximately 2 cm from the midline and just above the pubic symphysis (FIG. 16). Then, the mid-urethra is identified and two small transverse stab incisions are created approximately 0.5 cm at the marked suprapubic exit points. These exit sites should be close to the superior aspect of the pubic bone to avoid anatomic structures in the abdomen, inguinal area and lateral pelvic sidewall. The suprapubic incisions should be full thickness through the dermis in order to avoid excessive force while passing the delivery needles. A full thickness sagittal incision VI in the vaginal mucosa is created at the level of the mid-urethra approximately 1-2 cm in length, and then peri-urethral tunnels are created approximately 1-2 cm deep starting from the ipsilateral incision edge and aiming lateral towards the inferior edge of the pubic bone. This will create access for the delivery needles.

Next, the delivery needle is attached to the handle or handle assembly, as disclosed herein. While loading the delivery needle to the handle, the handle button and needle curvature should face upward. An audible "click" may be heard, indicating that the delivery needle is fully engaged in the handle.

Then, the sling assembly 200 can be placed. First, the tip of the delivery needle is inserted into the vaginal incision while opening the tunnel, by placing gentle outward traction on a clamp (e.g., Allis) or like device. The delivery needle should be guided gently with the non-dominant hand of the physician, and the needle tip can be advanced to puncture through the endopelvic fascia and into the retropubic space. Advancement of the delivery needle should be stopped when it punctures through the fascia. Next, the physician can confirm with an index finger of the non-dominant hand that the needle tip is just past the inferior edge of the pubic bone. The handle can be lowered so the distal end of the delivery needle contacts the posterior surface of the pubic bone and the trajectory of the needle tip is redirected to the targeted suprapubic exit point EP. Advancement of the delivery needle can continue, following the posterior surface of the pubic bone with the distal end of the delivery needle until the needle tip exits through the suprapubic incision exit point EP. The needle tip should protrude through the suprapubic incision allowing sufficient length to grasp the needle with the non-dominant hand. The delivery needle can then be pulled up until the trailing connection end, which is protruding through the vagina, is only protruding 2-3 cm out of the vaginal incision. This can ensure that the first delivery needle does not interfere with the second delivery needle pass.

The handle can then be disconnected from the delivery needle, as described with the various embodiments of the present invention (e.g., pressing release button 125 or pulling on release sleeve 106). The various above steps can be repeated for a second delivery needle on the contralateral side of the patient.

With the delivery needles in place, the physician can attach one end of the sling assembly 202 to a needle connection end protruding from the vagina. The connector 210 is generally attached when an audible "click" is heard. Next, the physician can orient the blue center markings 208 on the sheaths 206 facing outward, away from the urethra, and the second of the sling assembly connectors can be connected to the other needle connection end (e.g., second needle).

Once the sling assembly 200 is properly attached, the delivery needles and sling assembly 200 are pulled up through the suprapubic incisions EP one at a time. Once the sling assembly 200 exits the suprapubic region, the ends 210 can be secured with a clamp just below the level of the blue end markings 212 on the sheaths 206. The delivery needles and connectors 210 are then cut away, leaving behind the clamps, by cutting the sling assembly 200 at the blue marking 212 at each end of the sheath. The physician will then pull up on the cut ends of the sling assembly 200 to position it under the mid-urethra in a generally tension-free manner. The blue markings 208 on the sheaths can be used to indicate the center of the sling and can be used for centering the sling under the mid-urethra. Once desired placement is achieved, the clamps can be removed. Then sheaths 206 can be removed from the sling assembly 200 by pulling up on both sheath 206 ends simultaneously (e.g., thereby pulling them away from the overlapped section at or near the marking 208), leaving the mesh sling 202 in place.

Further adjustment of the sling 200 can be performed after the sheaths have been removed. An absorbable suture 204 in the mesh 202 of the sling assembly 200 allows for this adjustment of the sling. To loosen the sling 202, a blunt instrument, such as a clamp, can be placed between the sling 202 and the urethra. Pulling down the clamp or instrument loosens the sling as desired. To tighten the sling 202, an instrument, such as a clamp, can be placed across one end of the sling exiting the suprapubic incision EP. The sling 202 may then be rolled around the clamp to improve the grip, pulling up to tighten the sling as desired. If needed, this can be repeated on the contralateral side. Once optimal placement and tension is achieved, the sling 202 is cut at the level of the skin, pulling up on the incision edges with forceps. The suprapubic EP and vaginal incisions VI are then closed.

The various implants or systems, features and methods detailed herein are envisioned for use with many known implant and repair systems (e.g., for male and female), devices, features and methods, including those disclosed in U.S. Pat. Nos. 7,972,262, 7,500,945, 7,407,480, 7,351,197, 7,347,812, 7,303,525, 7,025,063, 6,691,711, 6,648,921, and 6,612,977, International Patent Publication Nos. WO 2008/057261 and WO 2007/097994, and U.S. Patent Publication Nos. 2011/0230704, 2011/0015480, 2011/0112357, 2010/0105979, 2010/0174134, 2010/0261955, 2008/0103351, 2005/0240076, 2002/151762 and 2002/147382. Accordingly, the above-identified disclosures are fully incorporated herein by reference in their entirety.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

The invention claimed is:

1. A delivery needle system, comprising:
   a needle including a proximal end portion and a distal end portion, the proximal end portion having a retention tip; and
   a handle assembly including a body portion and a release sleeve, the body portion having an interior needle channel and a retention clip, wherein the proximal end portion of the needle traverses the interior needle channel and is selectively releasable from the retention clip, with the release sleeve including a shaft portion having a retention arm to selectively seat within the body portion.

2. The system of claim 1, wherein the retention arm has at least one opening selectively engaged with the retention clip such that disengagement of the retention arm with the retention clip facilitates releasing the proximal end portion of the needle from the retention clip to permit disengagement of the needle from the handle assembly.

3. The system of claim 1, wherein the retention clip includes one or more extending fingers to selectively engage the proximal end portion of the needle.

4. The system of claim 3, wherein the one or more extending fingers includes one or more end tab portions.

5. The system of claim 1, wherein the retention clip includes one or more extending fingers capable of deforming to selectively release the proximal end portion of the needle.

6. The system of claim 1, wherein at least a portion of the needle is curved.

7. The system of claim 1, further including an actuator adapted to operatively release the proximal end portion of the needle from the retention clip.

8. The system of claim 7, wherein the actuator is a button device.

9. The system of claim 1, further including an elongate sling implant having an end connector to selectively connect with the distal end portion of the needle.

10. A delivery needle system, comprising:
    a needle including a proximal end portion and a distal end portion, the proximal end portion having a retention tip; and
    a handle assembly including a body portion, an actuator, and a separate sleeve portion, the body portion having an interior needle channel and a retention clip, wherein the proximal end portion of the needle traverses the interior needle channel and the retention tip is selectively engageable with the retention clip such that actuation of the actuator disengages the retention clip from the retention tip of the needle, the separate sleeve portion including an extending portion selectively engageable within the interior needle channel of the body portion.

11. The system of claim 10, further including a retention arm having at least one opening selectively engaged with the retention clip such that the actuator operatively engages the retention arm and facilitates releasing the retention tip of the needle from the retention clip to permit disengagement of the needle from the handle assembly.

12. The system of claim 10, wherein the retention clip includes one or more extending fingers to selectively engage the retention clip and the retention tip of the needle.

13. The system of claim 12, wherein the one or more extending fingers includes one or more end tab portions.

14. The system of claim 10, wherein at least a portion of the needle is curved.

15. The system of claim 10, wherein the actuator is a depressable button device.

16. The system of claim 10, further including an elongate sling implant having an end connector to selectively connect with the distal end portion of the needle.

17. The system of claim 10, wherein the retention tip of the needle is a bulbous tip portion.

18. A surgical implant system, comprising:
    an elongate sling implant having opposing end connectors;
    a needle including a proximal end portion and a distal end portion, the proximal end portion having a generally bulbous end tip; and
    a handle assembly including a sleeve portion, a body portion, an actuator, and an axially traversable release arm, the body portion having an interior needle channel and a retention clip, wherein the proximal end portion of the needle and the axially traversable release arm are selectively engageable with the retention clip such that actuation of the actuator disengages the release arm from the retention clip and correspondingly the proximal end portion of the needle from the retention clip, with a portion of the sleeve portion extending into and engageable within the body portion.

19. The system of claim 18, wherein the retention clip includes one or more deformable extending fingers.

20. The system of claim 18, wherein at least a portion of the needle is curved.

21. The system of claim 18, wherein the actuator is a depressable button device.

\* \* \* \* \*